United States Patent
Sandin et al.

(10) Patent No.: US 7,364,572 B2
(45) Date of Patent: Apr. 29, 2008

(54) PANT-SHAPED ARTICLE WITH IMPROVED FIT

(75) Inventors: Cecile Sandin, Molndal (SE); Katarina Eriksson, Lindome (SE); Sofia Hermansson, Vastra Frolunda (SE); Catarina Linner, Lindome (SE)

(73) Assignee: SCA Hygiene Products AB, Gothenburg (SE)

( * ) Notice: Subject to any disclaimer, the term of this patent is extended or adjusted under 35 U.S.C. 154(b) by 321 days.

(21) Appl. No.: 10/793,277

(22) Filed: Mar. 5, 2004

(65) Prior Publication Data

US 2004/0186452 A1    Sep. 23, 2004

Related U.S. Application Data

(60) Provisional application No. 60/452,536, filed on Mar. 7, 2003.

(51) Int. Cl.
*A61F 13/15* (2006.01)
(52) U.S. Cl. .......... 604/396; 604/385.01; 604/397; 604/385.25; 604/389; 604/392; 604/394; 604/385.27
(58) Field of Classification Search .......... 604/385.01, 604/385.25, 396, 387, 389, 392, 394, 385.27, 604/397; 2/73, 76, 78.1, 78.3
See application file for complete search history.

(56) References Cited

U.S. PATENT DOCUMENTS 4,906,243 A * 3/1990 Dravland ............. 604/394
5,034,007 A    7/1991 Igaue et al.
5,624,420 A    4/1997 Bridges et al.
6,010,586 A * 1/2000 Suprise ............... 156/73.1
6,607,515 B2 * 8/2003 Glaug et al. ........ 604/385.01
2002/0068919 A1    6/2002 Shinohara et al.
2002/0095127 A1* 7/2002 Fish et al. ............ 604/368
2003/0028165 A1    2/2003 Curro et al.
2004/0225270 A1    11/2004 Hermansson et al.

FOREIGN PATENT DOCUMENTS

EP    0 351 389 A1    1/1990

(Continued)

OTHER PUBLICATIONS

U.S. Appl. No. 10/792,895.

*Primary Examiner*—Jacqueline F. Stephens
(74) *Attorney, Agent, or Firm*—Buchanan Ingersoll & Rooney PC

(57) ABSTRACT

A pant shaped garment having a rear portion, a front portion, and a crotch portion, a waist opening with a waist edge and two leg openings bordered by a leg edge having a front part located generally on the front portion and a rear part located generally on the rear portion and on the crotch portion. Front and rear portions are mutually connected in two side joins which run from the waist opening to each leg opening. An elongated elastic element is pre-stretched along the rear part of the leg edge of each leg opening. The front portion comprises an elastically extensible material and the elongated elastic element constricts the rear part of the leg edge, thereby stretching the elastic material along the front part of the leg edge. The side joins exhibit a curvature in a direction towards the rear portion that increases in a direction from the waist opening towards the leg opening.

11 Claims, 3 Drawing Sheets

FOREIGN PATENT DOCUMENTS

| | | |
|---|---|---|
| EP | 0 761 194 A2 | 3/1997 |
| EP | 0 904 758 A2 | 3/1999 |
| EP | 1 106 154 A2 | 6/2001 |
| EP | 1 249 214 A2 | 10/2002 |

\* cited by examiner

PANT-SHAPED ARTICLE WITH IMPROVED FIT

CROSS REFERENCE TO RELATED APPLICATIONS

This application claims the benefit of U.S. Provisional Application No. 60/452,536, entitled "Pant-shaped Article with Improved Fit," filed on Mar. 7, 2003, the entire contents of which are hereby incorporated by reference.

BACKGROUND OF THE INVENTION

1. Technical Field

The invention pertains to a disposable garment in the form of a pant diaper or an underpant comprising an outer panty having a rear portion intended to be arranged over the buttocks of a user during use, a front portion intended to be arranged over the belly of a user during use, a crotch portion intended to be arranged in the user's crotch during use and, further, a waist opening with a waist edge and two leg openings each being bordered by a leg edge having a front part located generally on the front portion and a rear part located generally on the rear portion and on the crotch portion and wherein the rear portion and the front portion are mutually connected in two side joins which run from the waist opening to each leg opening.

2. Background Art

It has become increasingly more common to manufacture incontinence protectors in the form of pant diapers. Such pant diapers consist of an outer panty having an integral absorbent inner part. Alternatively, an outer panty can be used together with a separate incontinence shield which is temporarily attached inside the outer panty and which, thus, can be changed for a new incontinence shield while retaining the same outer panty. Both kinds of incontinence protectors are manufactured for infants as well as for incontinent adult persons.

The pant diapers and diaper pants concerned are of the disposable kind, implying that the pant diaper or diaper pant is intended to be discarded after use and not washed or otherwise restored for use. This means that the materials and production methods which are available are those which are cost efficient and do not result in articles having exceedingly high price. In particular, it must be possible to perform assembly steps and similar process operations at high speed, putting certain limitations on the choice of method. A difficulty in this respect is to make joins that closely resemble the seams that can be accomplished in garments made from conventional textile materials. Even if the assembly methods for disposable articles have been considerably improved over time, the joins in disposable articles are still stiffer and more apparent than is a seam in a garment for repeated use. This constitutes a special problem for pant diapers and underpants since such articles usually are joined at the sides. Thus, the side joins will be placed over the hips of the user during use and will often give rise to discomfort by chafing and pressing against the hip bone of the user. This is particularly bad for immobile and/or bedridden users for whom a static pressure against the skin, in the worst scenario, may cause a pressure ulcer. Another particular problem appears when the pant diaper or underpant is used under ordinary clothing such as pants or skirts, which often have their own side seams. There is then a great risk that the location of the side seams on the outer garment will mostly coincide with the location of the side join on the pant diaper or underpant. The double seams will naturally increase the risk of chafing and unpleasant pressure. Furthermore, the combination of garments is unwieldy and uncomfortable and it is hard to conceal the pant diaper or underpant under the outer garment.

A further problem in relation to pant diapers and underpants for supporting incontinence shields is that they have to provide a seal around the waist and thighs of the user so that leakage of body fluids is prevented. In order to achieve such gasketing, diaper pants and underpants are provided with elastic elements in the form of bands or strings that are arranged around the waist opening and around the leg openings. However, elastic elements may also cause unwanted chafing and pressure and, for this reason, there is a wish to minimise the use of elastic elements on disposable garments. In addition, for cost reasons and from a production point of view, it is favorable if the produced garment comprises as few components as possible.

Consequently, there still remains a need for a well-fitting and comfortable article in the form of a pant diaper or an underpant that can be worn under ordinary clothing without causing discomfort. There is also a need for a pant diaper or an underpant that has a comfortable fit and still affords good protection against leakage of body fluids at the leg openings.

OBJECTS AND SUMMARY

In accordance with embodiments of the invention, a garment of the kind mentioned in the introduction has been made which garment substantially removes the problems related to previously known such garments.

Garments in accordance with embodiments of the invention comprise an elongated elastic element being arranged with pre-stretching along the rear part of the leg edge of each leg opening and by the front portion comprising an elastically extensible material. The elongated elastic element constricts the rear part of the leg edge and thereby stretches the elastic material along the front part of the leg edge, whereby the side joins exhibit a curvature in the direction towards the rear portion and the amount of curvature increases in a direction from the waist opening to the leg opening.

Through the combination of an elastically extensible material in the front portion and an elastic element being arranged in a pre-stretched condition along the rear leg edges of the leg opening, several advantages are obtained. Hence, the rear elastic element constricts the rear leg edge and, further, exerts a pulling force on the material in the front portion. The pulling force is mainly directed in the extension of the rear elastic element whereby the principal stretching takes place in the front leg edge of each leg opening with the stretching force successively diminishing in a direction towards the waist edge. This means that the side joins of the pant diaper or the underpant are pulled towards the rear of the garment and take on the shape of a hook or the letter J. This is advantageous both because the side joins in this way will be arranged behind the hip bones of the user during use so that the risk of chafing and pressure over the hip bone is eliminated and because the risk of overlap between the side joins and the seams of a garment which is worn over the pant diaper or the underpant is very small. Moreover, the pant diaper or the underpant obtains an extraordinarily good fit, closely conforming to the shape of the user's body.

Further, it is an advantage to be able to exclude the use of an elastic element along the front leg edge of the leg openings. This provides a softer and more comfortable leg edge with minimal risk of chafing and uncomfortable pressure and brings about advantages in production since it saves material as well as a production step. Despite the lack of an elastic element along the front leg edges, a pant diaper or an underpant in accordance with an embodiment of the invention has very good fit and provides adequate sealing around the legs of the user. This is due to the elastic elements along the rear leg edges stretching and activating the elastic material in the front portion whereby an elastically contractile force is created also in the front leg edges when the pant diaper or underpant is being used. Because all of the front portion is elastically stretchable and the degree of stretching caused by the rear elastic element decreases in a direction towards the waist edge, the elastic seal along the front edges of the leg openings becomes soft and comfortable without wrinkles or other irregularities. A conventional elastic element in the form of a string or a band which is arranged along the front leg edge will exert a very localized pressure and will, in addition, wrinkle the material in the pant in a way which may give rise to chafing creases.

A further advantage of the embodiments of the invention is that the rear elastic elements pass over to the side joins in an elegant manner giving an attractive and tailored look. Particularly for adult users of incontinence protectors, it is an important aspect that the incontinence protectors imitate ordinary underwear as much as possible and that the impression of a "diaper" is toned down.

In accordance with one embodiment of the invention, the elongated elastic element is arranged on the portion of the leg edge that is located on the rear portion and extends all the way to the side join.

In one embodiment, the elongated elastic element extends advantageously over all of the segment of the rear part of the leg edge which is located on the rear portion and at least along a part of the segment of the rear portion of the leg edge which is located on the crotch portion.

Further, a garment in accordance with an embodiment of the invention may comprise an absorbent element having two long sides and two short sides wherein the absorbent element comprises an absorption body enclosed between a liquid permeable inner layer and a liquid impermeable barrier layer and is arranged at least in the crotch portion of the outer panty. Elastic elements may be arranged along the long sides of the absorbent element. In order to obtain good shaping of the absorption body, it is suitable that the elastic elements along the long sides of the absorbent element have a higher contractile force than the contractile force in the elastic elements along the rear part of the leg edge. This can be achieved by using elastic elements with different properties along the rear part of the leg edge and along the side edges of the absorption body. It is also possible to arrange the elastic elements with different degrees of pre-stretching. Another alternative is to use elastic elements consisting of one or several elastic part-elements wherein the higher contractile force is achieved by means of the number of elastic part-elements arranged along the long sides of the absorbent element being greater than the number of elastic part-elements arranged along the rear portion of the leg edge. Naturally, it is also possible to combine the different ways of achieving different elasticity in different areas of the elasticated portions of the pant diaper or diaper pant.

The elastic elements in the absorbent element in an embodiment of the invention can either constitute a part of the elastification of the leg edges of the outer panty or be completely separate elastic elements forming leakage barriers along all or a part of the length of the absorbent element. The elastic elements that are arranged along the absorbent element can be arranged in barrier flaps that preferably are designed so that during use they are raised from the liquid permeable cover on the inner side of the panty.

In one embodiment, a suitable material for the front portion of the outer panty is an elastic material laminate comprising two nonwoven layers and an elastic, perforated plastic film arranged between the nonwoven layers.

In a corresponding manner, the rear portion of the outer panty can comprise an elastic material laminate comprising two nonwoven layers and an elastic, perforated plastic film arranged between the nonwoven layers.

The crotch portion of the outer panty can comprise an essentially non-elastic material.

In one embodiment, it has been found to be suitable that the deviation of the side join from a straight line is at least 3 cm at the leg opening.

BRIEF DESCRIPTION OF THE DRAWINGS

In the following, the invention will be described more closely with reference to the figures which are shown in the appended drawings.

DETAILED DESCRIPTION OF THE PREFERRED EMBODIMENTS

Figure 1:
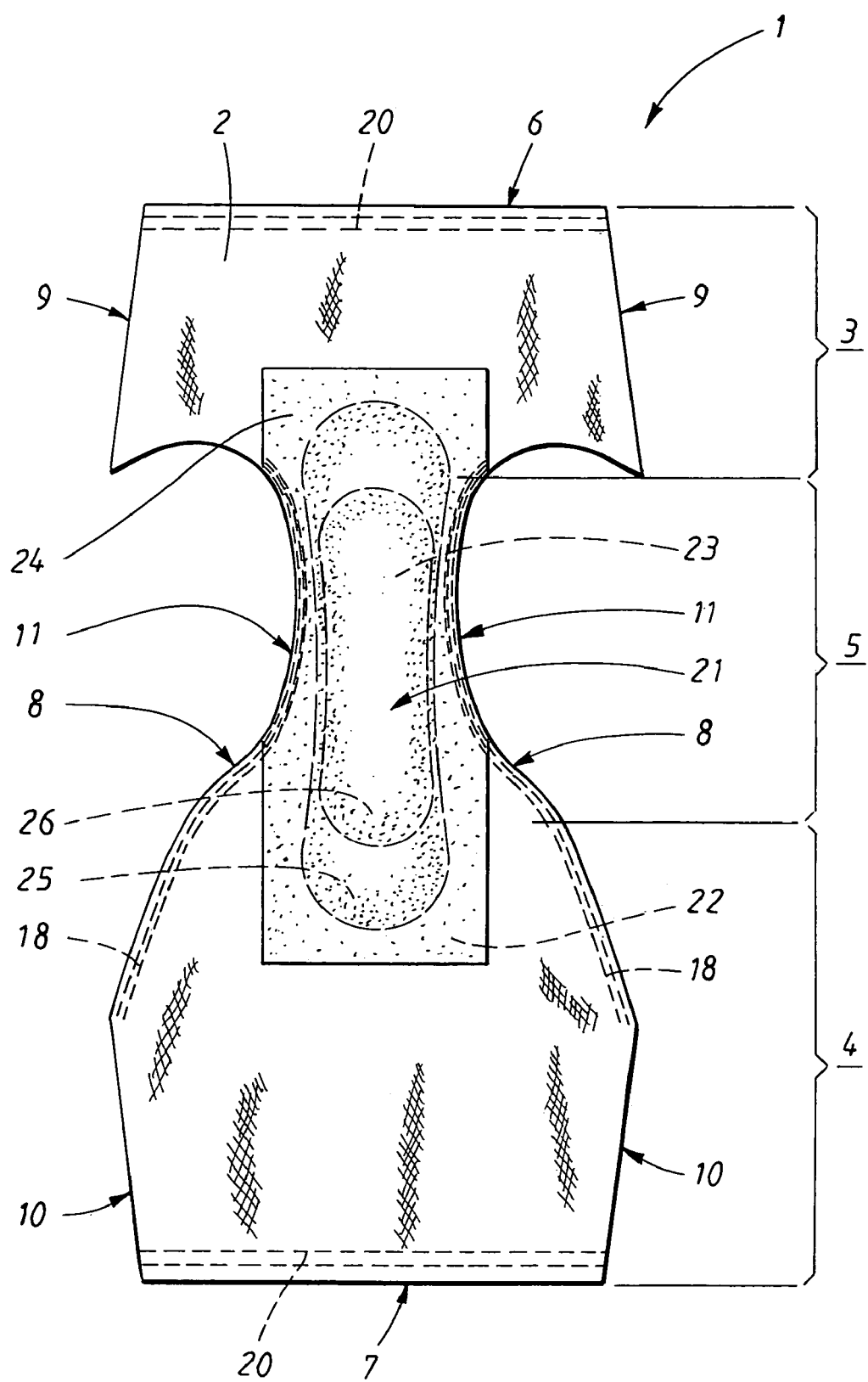
FIG. 1 shows a planar view of a pant diaper in accordance with an embodiment of the invention, seen from the side facing the user during use.
Figure 2:
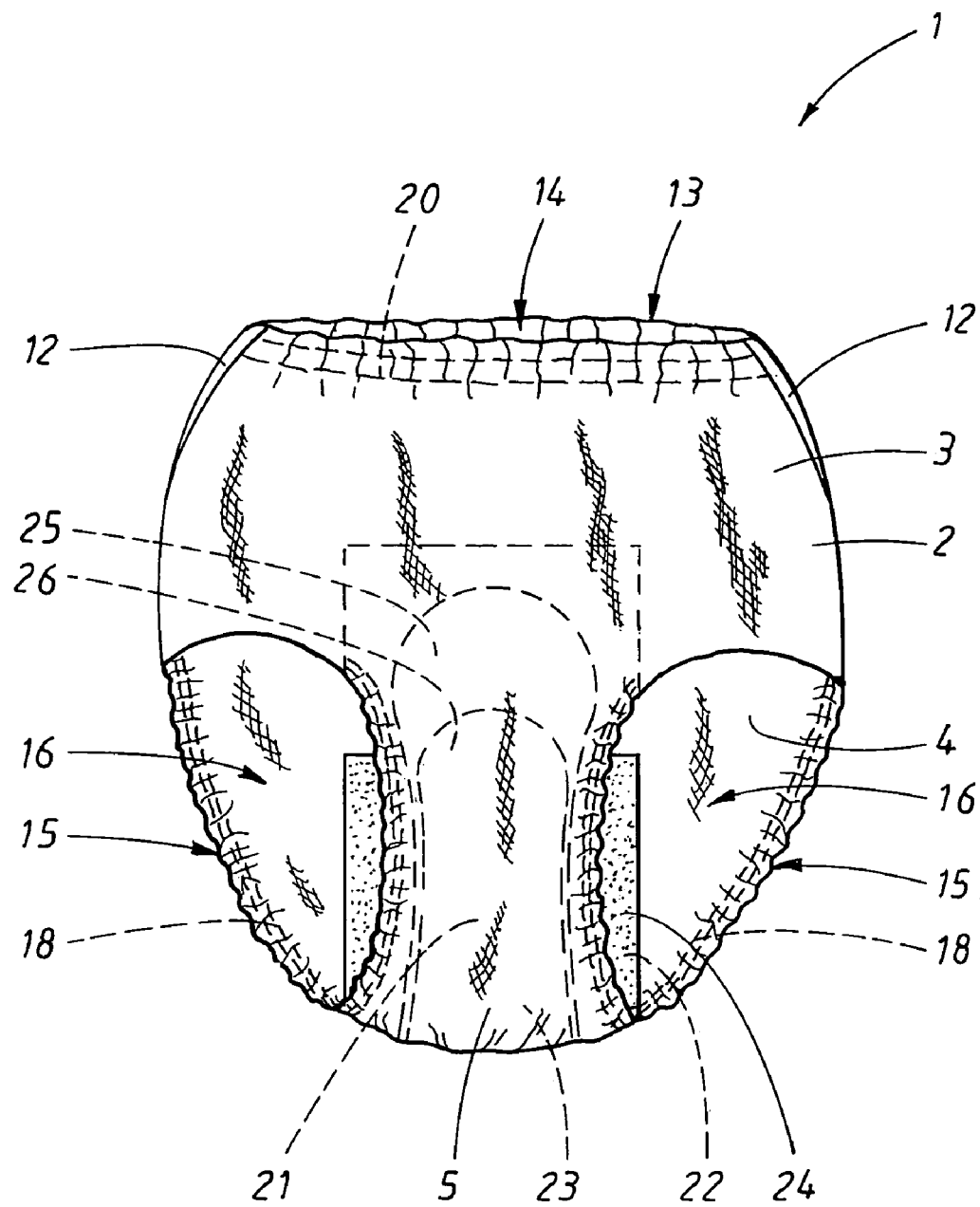
FIG. 2 shows a frontal view of the pant diaper in FIG. 1, as it appears in an assembled state.

For the sake of clarity, the pant diaper 1 in FIG. 1 is shown in a not fully-assembled, planar extended state. In FIG. 2, the pant diaper 1 is shown as it appears in an assembled state and without being exposed to stretching forces. The pant diaper comprises an outer panty 2 which can be divided into a front portion 3 which during use is intended to be facing to the front of the user and to be arranged over the stomach of the user, a rear portion 4 which during use is intended to be facing rearwards on the user and to be arranged over the buttocks of the user and a crotch portion 5 located between the front portion 3 and the rear portion 4 and which is intended to be placed in the user's crotch during use.

In the extended state shown in FIG. 1, the pant diaper 1 has a straight front end edge or front edge 6, a straight rear end edge or back edge 7 and two side edges 8 which each exhibit a front and a rear straight side segment 9, 10, and a curved leg segment 11 located between the straight side segments 9, 10. In the shown embodiment, the curved leg segments 11 have essentially the shape of a fishing hook with the hook part turned towards the front portion 3 of the pant diaper.

In an assembled state as shown in FIG. 2, the front side segment 9 of each side edge 8 is joined to the corresponding rear side segment in a side join 12. Thereby, the front edge 6 and the back edge 7 form a waist edge 13 which surrounds a waist opening 14 and the leg segments 11 of the side edges 8 form leg edges 15 which surround leg openings 16.

The side joins 12 are suitably made in a way to resist the pulling forces which arise when putting on and using the pant diaper but so that they can be torn apart when removing the used absorbent panty. An openable side join 12 does not have a greater cohesive ability than to allow the join to break at a lower force than that which is needed to tear the surrounding material in the absorbent panty. The side joins 12 can, for instance, be made by welding or by adhesive.

The outer panty 2 is at least partly formed from an elastic material. Thereby, at least the front portion 3 of the outer panty 2 is elastically stretchable. Suitable elastic materials include different types of elastic nonwoven materials. An elastic nonwoven material which is suitable for use in an absorbent panty in accordance with an embodiment of the invention is preferably able to be elastically stretched at least 80% and preferably at least 100% in the cross direction of the panty in order to provide sufficient elastic seal around the edges 15 of the leg openings 16 on the front portion 3. It is further advantageous if the elastic nonwoven material can also be elastically stretched in the length direction of the absorbent panty, i.e., in a direction perpendicular to the cross direction.

The elastic sheet material in the outer panty 2 can consist of a laminate of two or more layers. In the example shown in FIG. 1, the front portion 3 and the rear portion 4 consist of elastic material while the crotch portion 5 consists of an essentially non-elastic material. A material which is suitable for the purpose is a three-layer laminate with a nonwoven layer on each side of an apertured elastic film. Such a laminate provides an elastic and breathable outer panty. It is also possible to use other preferably breathable elastic materials. For instance, what are known as SMS-materials can be used. An SMS-material is a nonwoven laminate with a layer of spunbond nonwoven on each side of a meltblown nonwoven layer.

Elastic elements are arranged as leg elastic 18 around the leg openings 16 and as waist elastic 20 around the waist opening 14. When the outer panty 2 is formed from a laminate of two or more layers, the elastic elements 18, 20 are suitably attached between two such layers. The elastic elements 18 around the leg openings are only arranged on the crotch portion 5 and the rear portion 4, while the part of the leg edges 15 which extends over the front portion 3 is free from special elastic elements. Since the outer panty 2 comprises elastic material, it is not necessary to provide the waist opening 14 with special elastic elements 20, the elasticity in the outer panty 2 for many applications being sufficient for the diaper pant 2 to stay securely and comfortably in place and to fit tightly around the waist of the user. An alternative in order to obtain an enhanced elastic effect around the waist opening 14 is to fold the elastic material in the outer panty 2 so that a waist-band edge having an increased resistance to stretching is formed around the waist opening 14.

The elastic elements in the leg elastic 18 and the waist elastic 20 can be in the form of elastic threads, bands, or the like. If elastic threads or bands are used, two or more of these are often applied parallel with each other and will then constitute elastic part-elements of the elastic element. The material can be rubber, elastic foam, etc.

A core package 21 is attached inside the elastically stretchable outer panty 2; e.g., by means of adhesive or by welding. The core package 21 can be attached to the outer panty 2 over the entire mutual surface, or only over parts thereof. However, the core package 21 is preferably sufficiently well attached inside the outer panty 2 to prevent it from loosening or being moved out of place during use.

The core package 21 comprises a liquid barrier layer 22, an absorbent core 23, and a liquid-permeable inner layer 24. The core package 21 is attached with the liquid barrier layer 22 against the outer panty 2. FIG. 1 shows an absorbent core 23 consisting of two superposed absorbent layers 25, 26 wherein the lower absorbent layer 25 which is located closest to the liquid barrier layer 22 is somewhat larger than the upper absorbent layer 26 which is located closest to the inner layer 24. In the shown example, the core package 21 has an angular hour-glass shape in the plane, the planar shape of the core package being defined by the shape of the liquid barrier layer 22 and the liquid permeable inner layer 24 which together enclose the absorbent core 23. Naturally, it is possible to use core packages 21 having another planar shape, the liquid barrier layer 22 and the inner layer 24 may, for instance, have a more rounded hour-glass shape, a rectangular shape, a trapezoid shape, an oval shape, etc. Further, the core package 21 does not need to have the shape that is shown in the figure. Larger as well as smaller absorbent cores 23 can be used depending on the absorbent capacity which is desired in the pant diaper.

The liquid permeable inner layer 24 can comprise any material known for the purpose such as layers of nonwoven material, perforated plastic film, netting, tow, or similar material. The inner layer 24 may, of course, also comprise a laminate of two or more layers of the same or different material.

The liquid barrier layer 22 can consist of a liquid impermeable plastic film, a hydrophobic nonwoven layer or a nonwoven layer which has been treated to have liquid barrier properties, or any other flexible material layer which has the ability to resist liquid penetration. However, it may be an advantage if the liquid barrier layer 22 exhibits a certain breathability, i.e., allows passage of water vapour through the layer 22.

The absorbent core 23 can be formed from absorbent materials such as cellulose fluff pulp, tissue, absorbent foam, etc. It is also common that the absorbent core 23 comprises superabsorbents, i.e., polymeric materials which can absorb body fluids corresponding to several times their own weight while forming an aqueous gel. Such superabsorbents usually exist in the form of particles, but fibers, flakes, granules and film are also found. In addition, the absorbent core 23 may comprise non-absorbent components such as stiffening elements, shaping elements, binders, etc. Different kinds of fluid receiving and fluid distributing structures such as fibrous wadding, open-cell foam, wicking layers, or the like may also be included in the core package 21.

The different components which are included in the core package 21 may be connected to each other in a conventional manner, e.g., by gluing or welding with heat or ultrasonically. The core package 21 may comprise further components apart from those which have been described here, for instance the core package may comprise liquid transport layers, elastic elements, shape stabilizing elements, shaping elements, or the like. Even if the absorbent core has been shown having two absorbent layers 25, 26, alternative arrangements can be used. For some applications, e.g., a single absorbent layer may be sufficient, while other applications may require more than two absorbent layers. Thus, the design of the absorbent core can be adapted to the amount of liquid that the absorbent core is expected to absorb. Similarly, the kind of body fluids that are to be absorbed and the manner in which the body fluids are delivered to the absorbent core are naturally of importance for the size and properties of the absorbent core.

As is apparent from FIG. 1, the number of elastic part-elements in the elastic elements 18 is greater along the side edges of the absorbent package in the crotch portion than along the other parts of the leg edges 15. This is a suitable design in order to facilitate shaping and curving of the absorbent core 23, since the resistance to curving is greater in the absorbent core than in the more flexible surrounding parts of the pant diaper. The elastic elements 18 along the absorbent core 23 may either be components of the core package and be applied together therewith or be applied simultaneously with the other leg elastics of the outer panty 2.

As has previously been mentioned, FIG. 2 shows how the one embodiment of a pant diaper appears before it is put on. All elastic elements and components are substantially non-stretched. Since the leg elastic 18 and the waist elastic 20 are attached to the outer panty 2 in a stretched state, they contract the material in the outer panty 2 when the stretching ceases. This means that the pant diaper 1 has a somewhat wrinkled waist edge 13 before being put on and that the leg edges 15 are wrinkled in the crotch portion 5 and in the rear portion 4.

Figure 3:
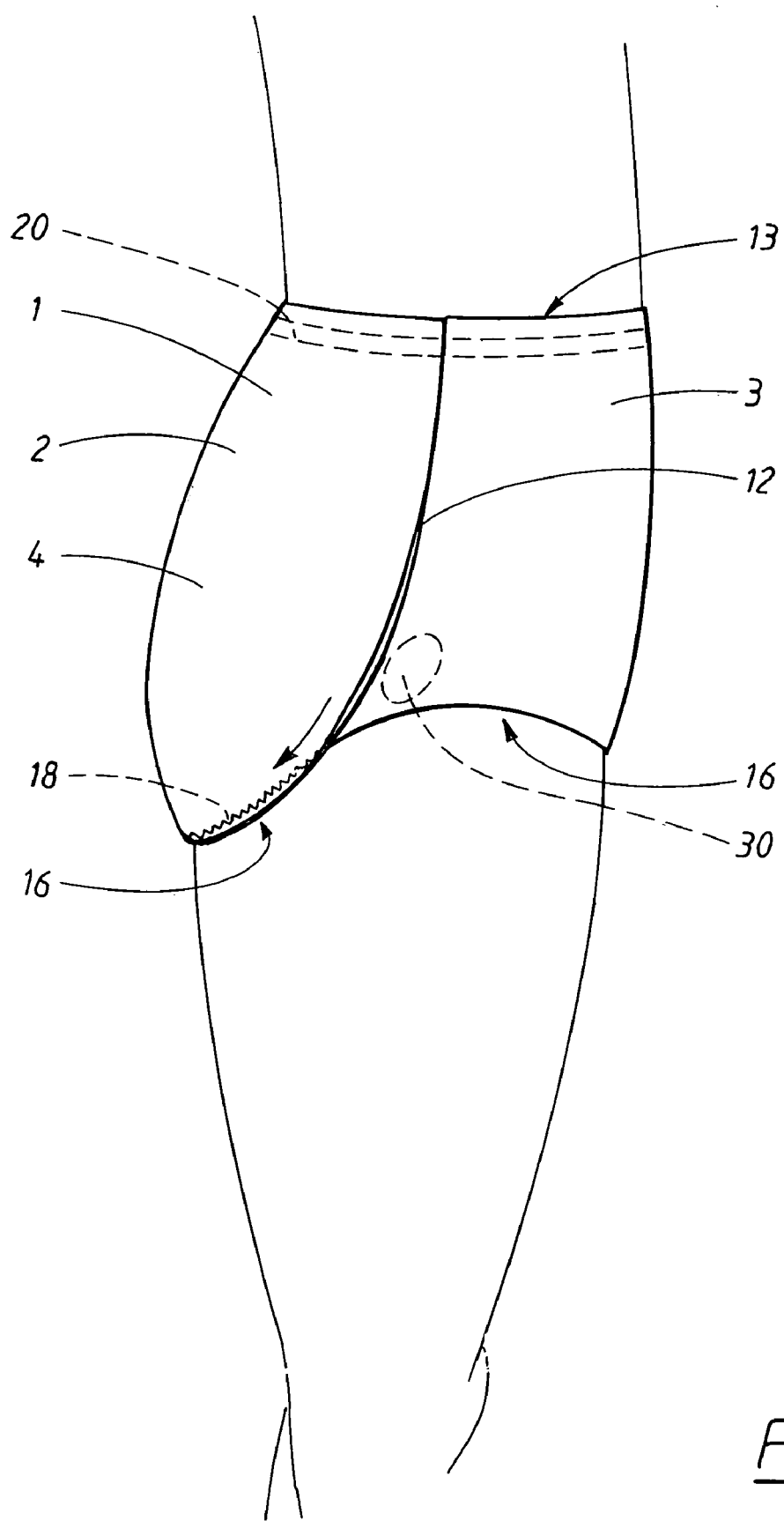
FIG. 3 shows a side view of the pant diaper in FIG. 1, as it appears during use.

In FIG. 3, the pant diaper 1 is shown while being worn by a user. Due to the tension in the leg elastic 18 along the leg edge 15 on the crotch portion 5 and the rear portion 4 being greater than the resistance to stretching in the elastic material of the outer panty 2 on the front portion 3, the part of the side join 12 which is located closest to the leg opening 16 is pulled rearwards on the pant diaper 1. In this manner, the side join 12 is given a curved shape with a curve radius which increases in a direction from the waist edge 13 towards the leg edge 15. The curving of the side join 12 results in the side join 12 being placed behind the hip bone 30 of the user when the pant diaper is put on. As has been mentioned earlier, this is a major advantage since the risk of chafing and unpleasant pressure from the side join 12 is thereby eliminated. Furthermore, an overlap between the side join 12 and any side seams on a garment which is worn over the pant diaper 1 is avoided.

The absence of a particular elastic element along the leg edge 15 on the front portion 3 is advantageous from several aspects. Above all, it gives the pant diaper an exceptionally good fit with a smooth and comfortable seal around the front part of the user's thighs. The risk of chafing on the front and insides of the thighs is completely eliminated and the pant diaper can be discreetly worn under normal clothing.

Within the scope of the invention, it is possible to design the absorbent portion of the pant diaper in a different manner from that which has been described. The shape and size of the absorbent core, as well as the shape and size of the liquid barrier layer and the inner layer can, of course, be varied. It is also possible to completely exclude the liquid barrier layer. In such a case, it is generally suitable that the material in the pant diaper, at least within the area of the absorbent core, can resist liquid penetration.

Moreover, the leg elastics may be arranged only along, for instance, the part of the leg edge that extends over the rear portion or along the leg edge on the rear portion and a part of the crotch portion.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A pant shaped garment in the form of a pant diaper or an underpant comprising:
   an outer panty having a rear portion intended to be arranged over the buttocks of a user during use;
   a front portion intended to be arranged over the belly of a user during use, the front portion comprises an elastically extensible material;
   a crotch portion intended to be arranged in the crotch of the user during use;
   a waist opening with a waist edge;
   two leg openings each being bordered by a leg edge having a front part located generally on the front portion and a rear part located generally on the rear portion and on the crotch portion and wherein the rear portion and the front portion are mutually fastened to each other with joints which run from the waist opening to each leg opening; and
   an elongated elastic element arranged with pre-stretching along the rear part of the leg edge of each leg opening and the elongated elastic element causes a constriction in the rear part of each of the leg edges when the garment is being worn;
   wherein the garment is constructed such that the constrictions cause the joints to exhibit a curvature in a direction towards the rear portion and stretch the elastic material along the front part of the leg edges, whereby the curvature increases in a direction from the waist opening towards the leg opening.

2. The garment according to claim 1, wherein the elongated elastic elements are arranged on the portion of the respective leg edge which is located on the rear portion and extends all the way to the respective joint.

3. The garment according to claim 2, wherein the elongated elastic elements extend over all of the segment of the rear part of the leg edge which is located on the rear portion and at least along a part of the segment of the rear part of the leg edge which is located on the crotch portion.

4. The garment according to claim 1, further comprising an absorbent element having two long sides and two short sides wherein the absorbent element comprises an absorption core enclosed between a liquid permeable inner layer and a liquid impermeable barrier layer and is arranged at least in the crotch portion of the outer panty.

5. The garment according to claim 4, further comprising elastic elements arranged along the long sides of the absorbent element.

6. The garment according to claim 5, wherein the elastic elements along the long sides of the absorption element have a higher contractile force than the contractile force in the elastic elements along the rear part of the leg edge.

7. The garment according to claim 6, wherein the elastic elements comprise one or several elastic part-elements wherein the higher contractile force is achieved by means of the number of elastic part-elements arranged along the long sides of the absorbent element being greater than the number of elastic part-elements arranged along the rear portion of the leg edge.

8. The garment according to claim 1, wherein the front portion of the outer panty comprises an elastic material laminate comprising two nonwoven layers and an elastic, perforated plastic film arranged between the nonwoven layers.

9. The garment according to claim 8, wherein the rear portion of the outer panty comprises an elastic material laminate comprising two nonwoven layers and an elastic, perforated plastic film arranged between the nonwoven layers.

10. The garment according to claim 1, wherein the crotch portion of the outer panty comprises an essentially non-elastic material.

11. The garment according to claim 1, wherein the deviation of the side join from a straight line is at least 3 cm at the leg opening.

* * * * *